United States Patent [19]

Rose

[11] Patent Number: 4,640,621

[45] Date of Patent: Feb. 3, 1987

[54] TRANSMISSOMETER AND OPTICAL ELEMENTS THEREFOR

[75] Inventor: Thomas H. Rose, County of Wake, N.C.

[73] Assignee: Eastern Technical Associates, Inc., Raleigh, N.C.

[21] Appl. No.: 505,535

[22] Filed: Jun. 17, 1983

[51] Int. Cl.[4] .......................... G01J 1/02; G01N 21/00
[52] U.S. Cl. .................................... 356/434; 356/243; 356/438
[58] Field of Search ............... 356/433, 434, 437, 438, 356/439, 243

[56] References Cited

U.S. PATENT DOCUMENTS

| | | | |
|---|---|---|---|
| 3,850,529 | 11/1974 | Brugger | 356/207 |
| 3,994,601 | 11/1976 | Brugger | 356/201 |
| 3,997,271 | 12/1976 | Brugger et al. | 356/201 |
| 4,017,193 | 4/1977 | Loiterman | 356/438 X |
| 4,050,814 | 9/1977 | McFadden | 355/71 |
| 4,126,396 | 11/1978 | Hartmann et al. | 356/434 |
| 4,222,641 | 9/1980 | Stolov | 353/84 |
| 4,247,205 | 1/1981 | Typpo | 356/438 |
| 4,294,524 | 10/1981 | Stolov | 353/84 |
| 4,333,724 | 6/1982 | Honma | 356/437 |
| 4,364,639 | 12/1982 | Sinclair et al. | 350/331 R |
| 4,422,729 | 12/1983 | Suzuki et al. | 350/336 |
| 4,432,649 | 2/1984 | Krause | 356/438 |

Primary Examiner—Michael R. Lusignan
Attorney, Agent, or Firm—Bell, Seltzer, Park & Gibson

[57] ABSTRACT

A transmissometer includes electronic shutters for interrupting the transmitted and reference light beams at selected locations and at selected time intervals for establishing the various modes of operation of the transmissometer. The electronic shutters take the form of liquid crystal displays that are selectively energizable to either a clear or an opaque condition. The transmissometer also includes an electronic stepwise light attenuator located in the path of the light beams. The attenuator includes a body and multiple liquid crystal display segments uniformly distributed throughout the body, with the segments being independently energizable to provide stepwise opacity.

15 Claims, 13 Drawing Figures

ZERO MODE
Fig-3

CALIBRATION MODE
Fig-4

SPAN MODE

Fig-5

MEASUREMENT MODE

TRANSMISSOMETER AND OPTICAL ELEMENTS THEREFOR

BACKGROUND OF THE INVENTION

1. Field of the Invention

The present invention relates to transmissometers for measuring the opacity of fluid samples. In particular embodiments the invention relates to a transmissometer incorporating electronic shutters and an electronic stepwise light attenuator which are selectively actuated to place the transmissometer in the several light transmission modes necessary for opacity measurement, calibration and correction for drift.

2. Description of the Prior Art

Environmental considerations have given rise to regulatory requirements for the continuous monitoring of the opacity of smokestack effluents. The most reliable systems for providing this continuous monitoring are know as double-pass transmissometers. These devices include a light source on one side of the smokestack and an aligned retroreflector on the other side. A collimated light beam passes through the smokestack, is reflected by the retroreflector so that it passes through the smokestack again and then is picked up at selected time intervals by a photodetector whose output signals are representative of the opacity of the effluent through application of Beer's Law.

It is well known that transmissometers must be calibrated, preferably by calibration to a zero attenuation reference and upscale attenuation references. These conditions are achieved by directing a reference light beam from the source to the photodetector without allowing the beam to enter the smokestack.

A further consideration is that the transmissometer must be provided with means for compensating for "drift" caused by variations in the intensity of the light source, changes in the sensitivity of the photodetector, temperature changes, etc.

In order to deal with the calibration and drift problems, devices of the prior art have incorporated mechanical means for diverting optical paths and attenuating light in the optical path. These mechanical aspects of prior devices have proven quite complicated, and provide an aspect of unreliability that is undesirable in transmissometers which are usually placed at remote locations.

SUMMARY OF THE INVENTION

In accordance with the present invention, there is provided a transmissometer that overcomes the disadvantages associated with transmissometers incorporating the above-mentioned mechanical components.

In one aspect, the invention may be defined as an optical device that establishes a transmitted beam and a reference beam and directs the transmitted beam into a sample where it is attenuated. The device also includes a detector for generating a signal representative of a condition of the beams when they are incident on the detector, and an electronic stepwise light attenuator located in the path of the light constituting the reference beam. The attentuator comprises a body and multiple liquid crystal display segment sets distributed throughout the body, with the segment sets being independently energizable to place each segment set in either a clear or an opaque condition.

The display segment sets preferably comprise a grid of relatively long, thin segments that are substantially uniformly distributed throughout the body so as to provide uniform dispersion of the radiation incident thereon. Other geometric patterns such as concentric circles, radiating lines and spirals may be used.

In another aspect the invention comprises a transmissometer for continuously monitoring the opacity of gases passing through a duct. The transmissometer includes a primary unit adapted for mounting on one side of the duct to deliver a transmitted light beam across the duct and to establish a reference beam, and a retroreflecting unit adapted for mounting on the opposite side of the duct to reflect the transmitted beam back to the primary unit. The transmissometer includes a plurality of beam shutters located at selected points in the optical paths of the transmitted and reference beams for interrupting the beams to establish various transmissometer modes of operation necessary to measure the gas opacity, calibrate and account for drift. The shutters comprise electronic liquid crystal displays selectively energizable by on-off pulses to produce either a clear or an opaque condition at each display at selected time intervals. The transmissometer may also include an electronic stepwise light attenuator, as defined above, located at a selected location in the path of the light beams.

BRIEF DESCRIPTION OF THE DRAWINGS

The invention will be more fully understood from the following detailed description thereof taken in connection with the accompanying drawings, in which.

DETAILED DESCRIPTION OF THE INVENTION

While the present invention will be described hereinafter with particular reference to the accompanying drawings, it is to be understood at the outset of the description which follows that it is contemplated that the present invention may be varied in specific detail while still achieving the desirable characteristics and features of the present invention. Accordingly, the description is to be understood as a broad enabling teaching directed to persons skilled in the applicable arts, and is not be be understood as restrictive.

Figure 1:
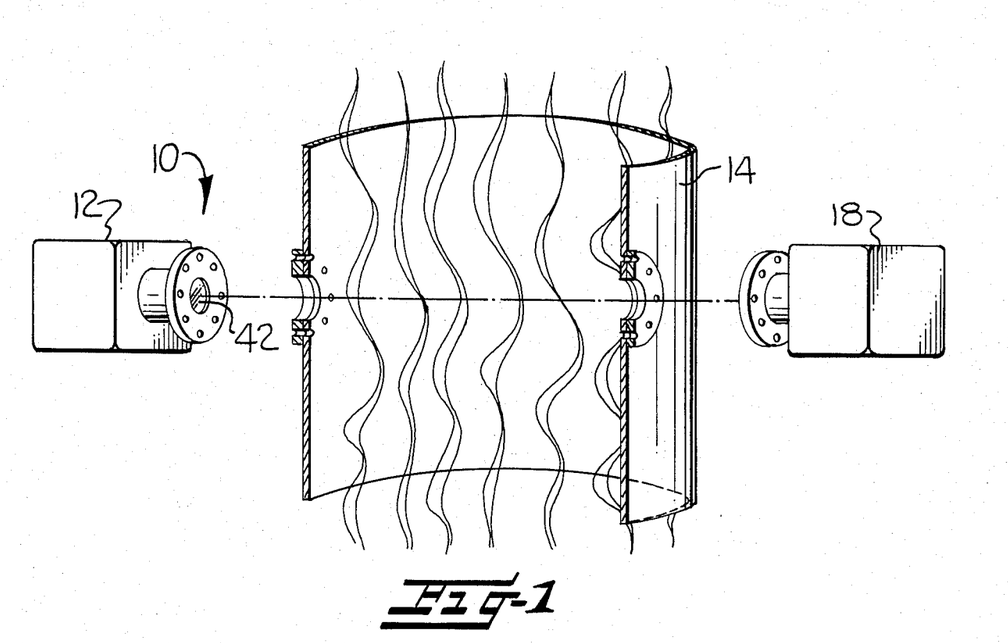
FIG. 1 is a perspective view of an exploded transmissometer of the invention in operative position with respect to a smokestack for continuously monitoring the opacity of the smokestack effluents.

Referring to the drawings, and particularly to FIG. 1, there is shown a double-pass transmissometer 10 constructed in accordance with the present invention. Transmissometer 10 includes a primary unit 12 adapted for mounting on one side of a smokestack 14 and a retroreflecting unit 18 adapted for mounting on the opposite side of the smokestack.

Referring to the schematic illustration of FIG. 2, the transmissometer will now be described initially without reference to the electronic shutters and stepwise attenuator so as to first set forth the paths of the light beams. Primary unit 12 includes a light source 20 that emits light that is collimated into a light beam 22 by means of optical means 24 of any suitable type known in the art, for example, a condensing lens and aperture arrangement.

Light beam 22 next falls on a beam splitter in the form of a partially reflective mirror 32 that is inclined to beam 22. In the illustrated embodiment, mirror 32 is inclined at 45° with respect to beam 22 and is half silvered so as to reflect approximately one half of beam 22 in a direction normal to beam 22 to establish a transmitted beam 36. The remaining half of beam 22 passes directly through mirror 32, remaining colinear with beam 22, and establishes a reference beam 40.

The transmitted beam 36 is projected across smokestack 14 through first and second windows 42, 44 and is incident upon a retroreflector 48, for example, a corner cubed mirror that reflects light incident thereon back along its direction of incidence. The reflected transmitted beam travels back through smokestack 14 to the beam splitter where approximately one half of the beam passes through the splitter in the direction of a photodetector 50 and associated photopic filter 51 of a type well known in the art.

The reference beam 40, after being split from beam 22, enters a branch 52 that is oriented substantially normal to the path of the transmitted beam. Branch 52 includes a front surface mirror 56 that is postioned substantially normal to the reflected beam for reflecting the reference beam back to the beam splitter where a portion thereof is reflected to photodetector 50 along a path substantially colinear with that of the transmitted beam.

Figure 2:
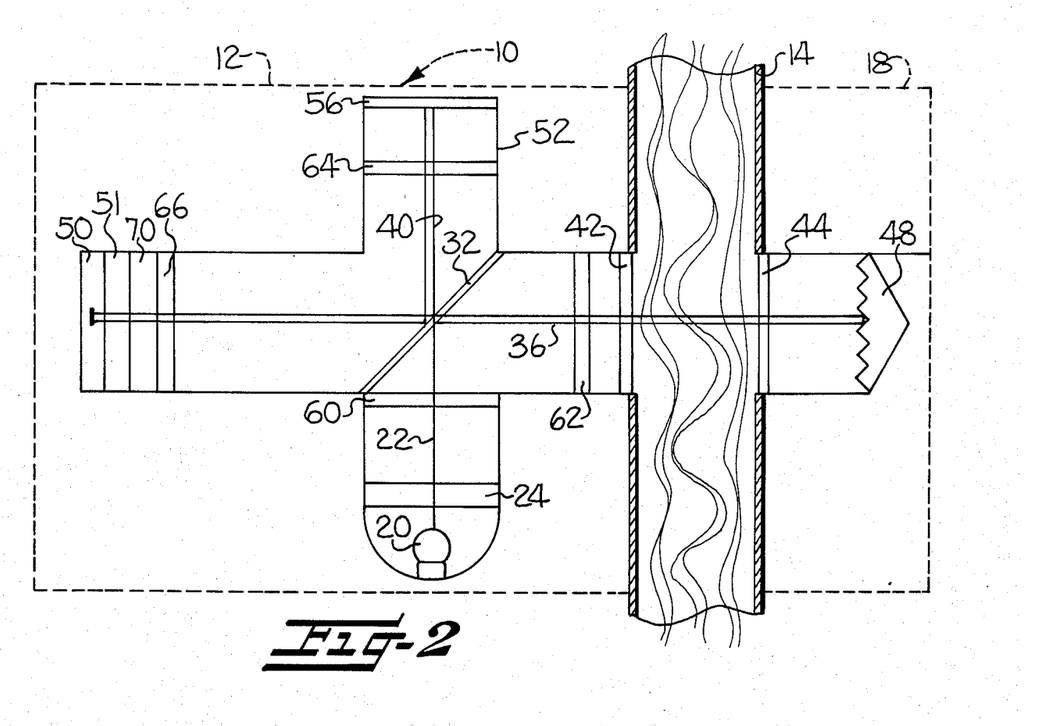
FIG. 2 is a schematic representation of a transmissometer of the invention with all of the electronic shutters and the electronic stepwise attenuator in the clear condition.

The foregoing description of the beam paths is solely for the purpose of setting forth some of the elements of the transmissometer 10 and to establish the uninterrupted light paths that would occur in a situation where all of the electronic shutters and the stepwise attenuator are clear as represented in the schematic illustration of FIG. 2. However, in the various modes of operation discussed below, the electronic shutters and stepwise attenuator are actuated in various fashions to provide opaque conditions at selected points in the light paths.

Transmissometer 10 includes four electronic shutters as follows: (a) a chopper shutter 60 located between the light source 20 and the beam splitter; (b) a system shutter 62 located in the path of the transmitted beam between the beam splitter and the retroreflector; (c) a zero shutter 64 located in the path of the reference beam between the beam splitter and the photodetector; and (d) a span shutter 66 located in the paths of the reference beam and the reflected transmitted beam just prior to their incidence upon the photodetector.

Each of the electronic shutters comprises a liquid crystal display that is selectively energized or non-energized to place the display in either a clear or an opaque condition. The shutters may take a form similar to that of Model No. 39992606 displays manufactured by Hamlin Company of Lake Mills, Wis. which incorporate a pair of parallel polarized plates separated by a liquid crystal. In the non-energized state the crystal rotates the incident light 90° to establish an opaque condition for the display. In the energized state the light is not rotated by the crystal, thus establishing a clear condition.

Figure 7:
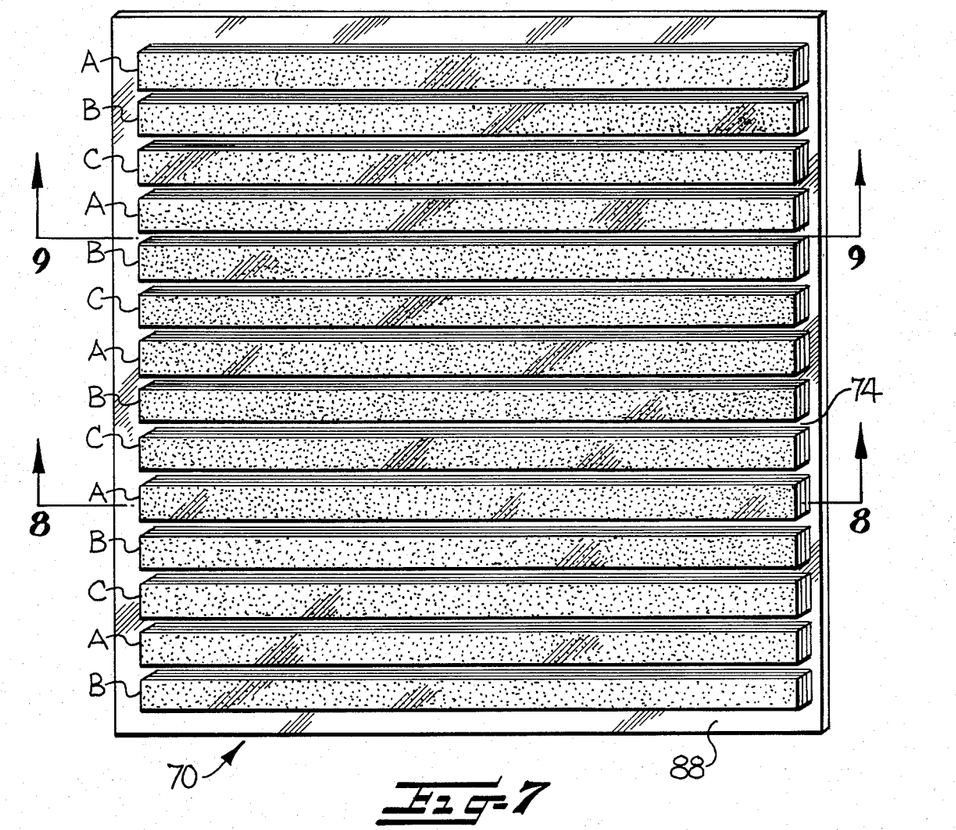
FIG. 7 is a plan view of a most preferred embodiment of the variable opacity stepwise attenuator of the invention.

Transmissometer 10 also includes an electronic stepwise light attenuator 70 located proximate to photodetector 50 in the path of both the reference beam and the reflected transmitted beam. As best shown in FIG. 7, attenuator 70 comprises a planar body incorporating multiple liquid crystal display segment sets A,B,C that are distributed throughout the body. The segment sets are independently energizable to place each segment set in either a clear or an opaque condition, thereby providing a light attenuator having stepwise opacity determined by the conditions of the segment sets. In the illustrated embodiment, attenuator 70 is substantially rectangular and is divided into four substantially equal portions of surface area. The first portion comprises the clear strip areas 74 residing between the respective liquid crystal display segments. The remaining three areas are formed by the three sets of alternating rows of display segments.

When all three segment sets A,B,C are in a clear condition, attenuator 70 is substantially clear, i.e., 0% opaque. By energizing the segment sets so that one is opaque, the attenuator becomes 25% opaque; two opaque segment sets render the attenuator 50% opaque; and three opaque segment sets render the attenuator 75% opaque.

Figure 8:
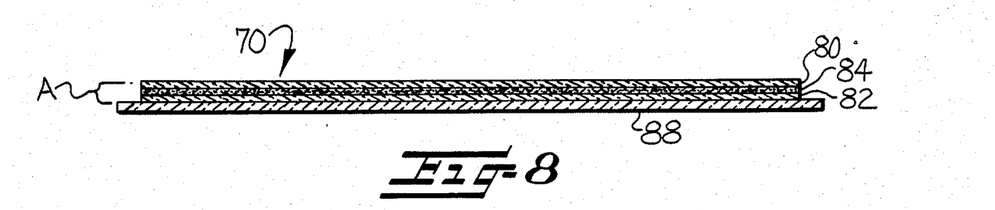
FIG. 8 is a sectional view taken substantially along line 8—8 of FIG. 7.
Figure 9:
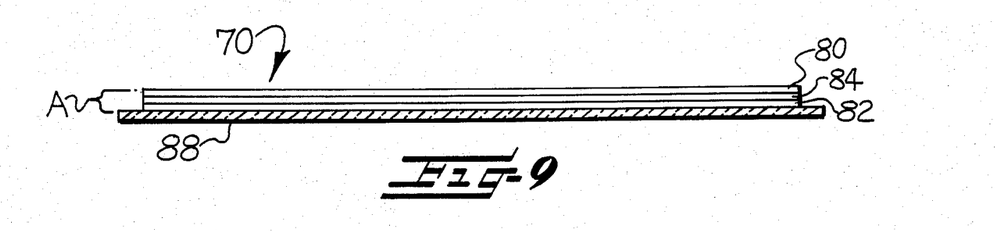
FIG. 9 is a sectional view taken substantially along line 9—9 of FIG. 7.

The display segment sets A,B,C may be formed from parallel polarized plates 80, 82 (FIG. 8) separated by a liquid crystal 84 as explained above in connection with shutters 60, 62, 64, 66. The display segments are mounted on a clear plate 88 that serves as the carrier plate for the displays and establishes the clear one-fourth area of attenuator 70 (FIGS. 7 and 9). In the illustrated embodiment, segments A,B,C are relatively long, thin segments uniformly distributed in alternating fashion throughout the body of attenuator 70 so as to provide uniform dispersion of the light incident thereon.

Figure 10:
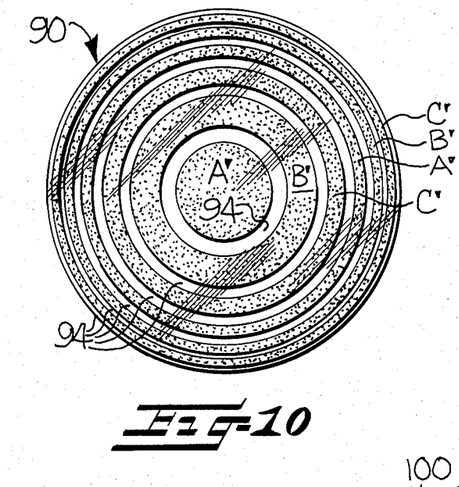
FIGS. 10–12 are plan views of first, second and third alternative embodiments of the variable opacity stepwise attenuator of the invention.
Figure 11:
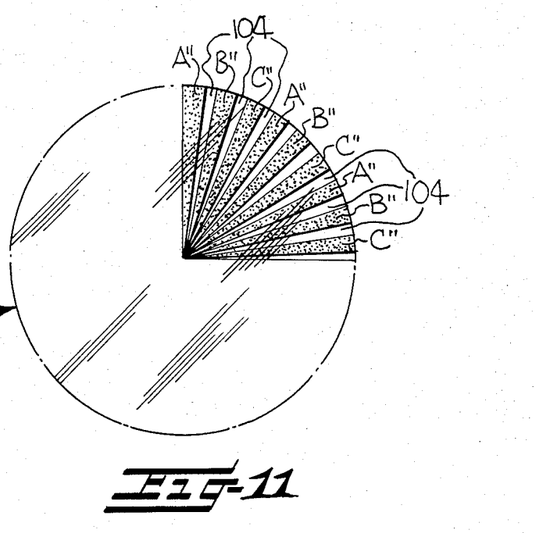
Figure 12:
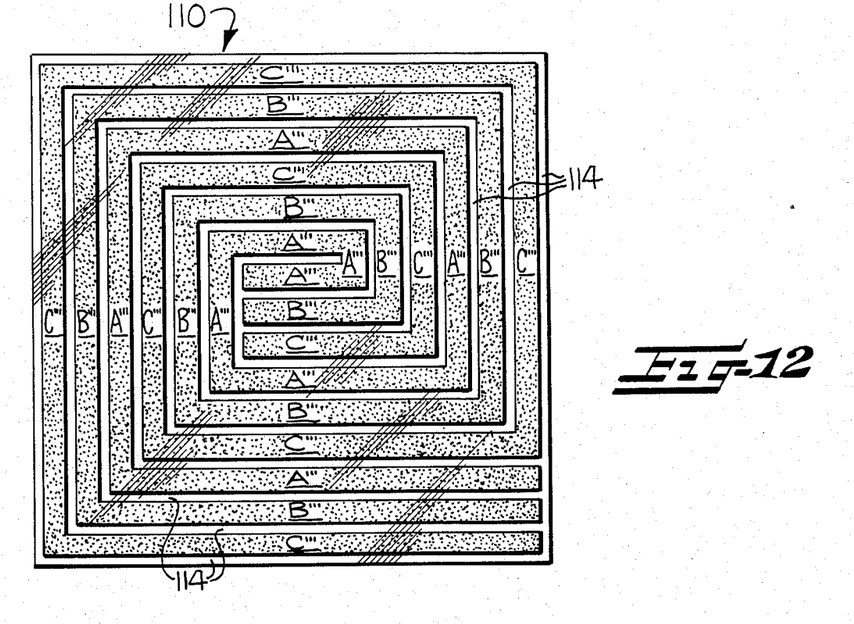

FIGS. 10–12 illustrate three alternative embodiments of stepwise light attenuators constructed in accordance with the present invention.

FIG. 10 shows an attenuator 90 comprising a planar body incorporating liquid crystal display segments in the form concentric circles. The segments define three segment sets A',B',C' that are independently energizable.

FIG. 11 shows an attenuator 100 having multiple liquid crystal display segments in the form of radiating strips. The segments define segment sets A", B", C" that are independently energizable.

FIG. 12 illustrates yet another attenuator 110 incorporating spirals formed from liquid crystal displays. Each spiral defines segments and independently energizable segment sets A''', B''', C''', each of said sets being a complete spiral.

Each of the attenuators of FIGS. 10–12 is illustrated as having three independently energizable portions comprising one fourth of the surface area of the attenuator with remaining portions 94, 104, 114 comprising the remaining one-fourth surface area, such that stepwise attenuation of 0%, 25%, 50%, 75% opacity is achieved. It will be appreciated that the attenuators illustrated in FIGS. 7 and 10–12 have been shown as divided into one fourth areas; however, other equal divisions of the area or unequal divisions may be desirable and are within the spirit and scope of the invention.

While attenuator 70 has been illustrated as positioned immediately ahead of photodetector 50, it may be positioned anywhere in the path of the light that constitutes reference beam 40. For example, attenuator 70 may be placed in the branch containing light source 20 in a position adjacent chopper shutter 60 in which case it may serve to block light beam 22 (which is the basis for and therefore constitutes reference beam 40.) Attenuator 70 may also be placed in branch 52 that contains mirror 56 and zero shutter 64. It will be appreciated that when attenuator 70 is so placed in branch 52 the reference beam 40 will make a double pass through the attenuator.

Figure 3:
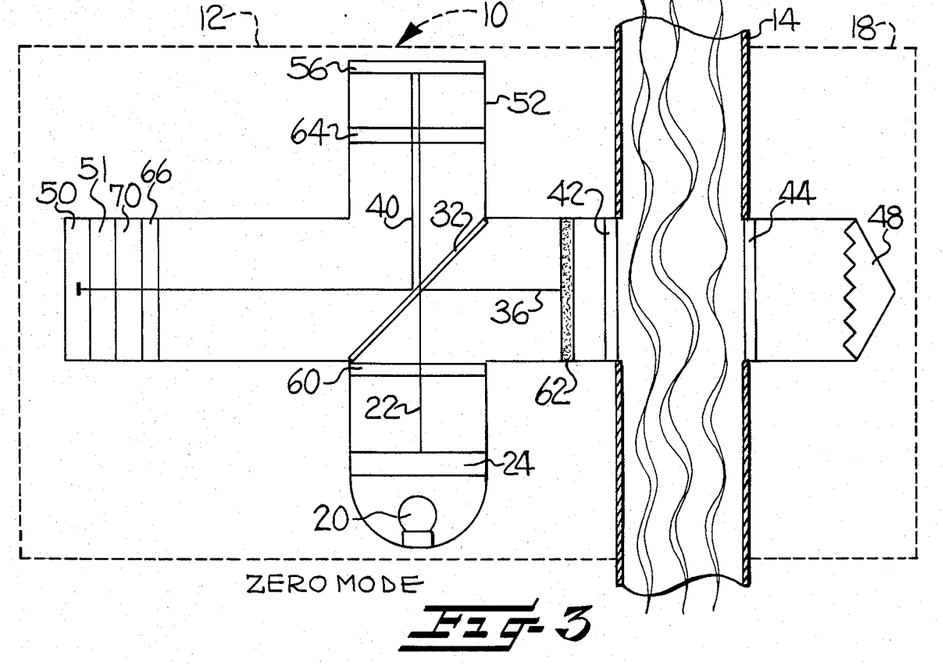
FIG. 3 is a view similar to FIG. 2 showing the transmissometer in the zero mode.

The various operating modes of transmissometer 10 are illustrated in FIGS. 3–6. FIG. 3 schematically illustrates the zero mode wherein the transmitted light beam is blocked by means of the opaque condition of system shutter 62. In the zero mode, as well known to those skilled in the art, the reference beam is allowed to impinge unattenuated upon the photodetector to provide a reference for zeroing the system.

Figure 4:
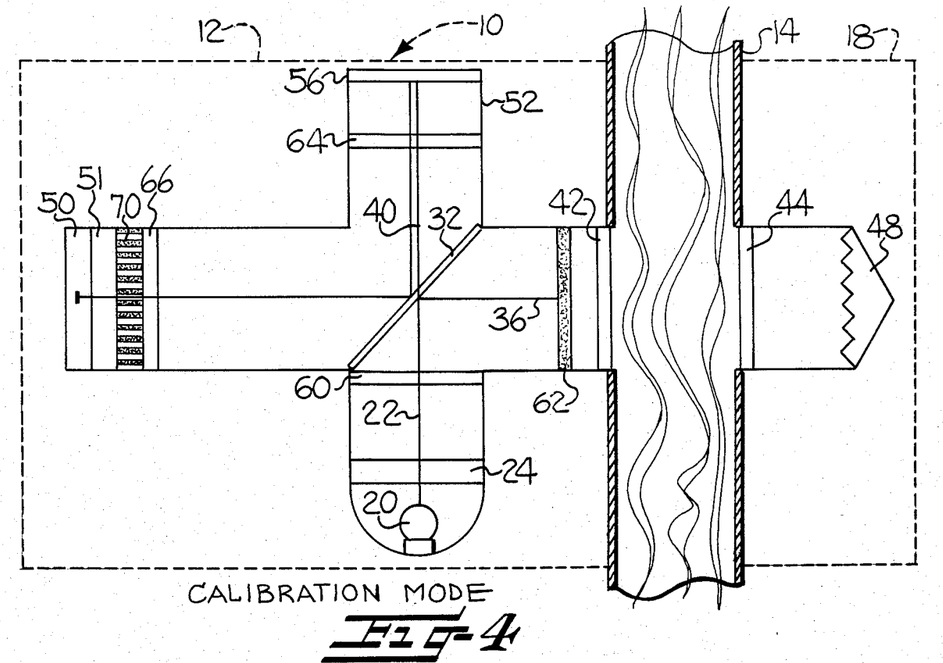
FIG. 4 is a view similar to FIGS. 2 and 3 showing the transmissometer in a calibration mode for an upscale check.

FIG. 4 illustrates a calibration mode for performing an upscale check on the system. In the calibration mode system shutter 62 blocks the transmitted beam. The calibration mode differs from the previously discussed zero mode in that stepwise attenuator 70 is selectively actuated to one of the stepwise opacity conditions, for example 25%, 50% or 75% opaque, so as to permit an upscale check of the system.

Figure 5:
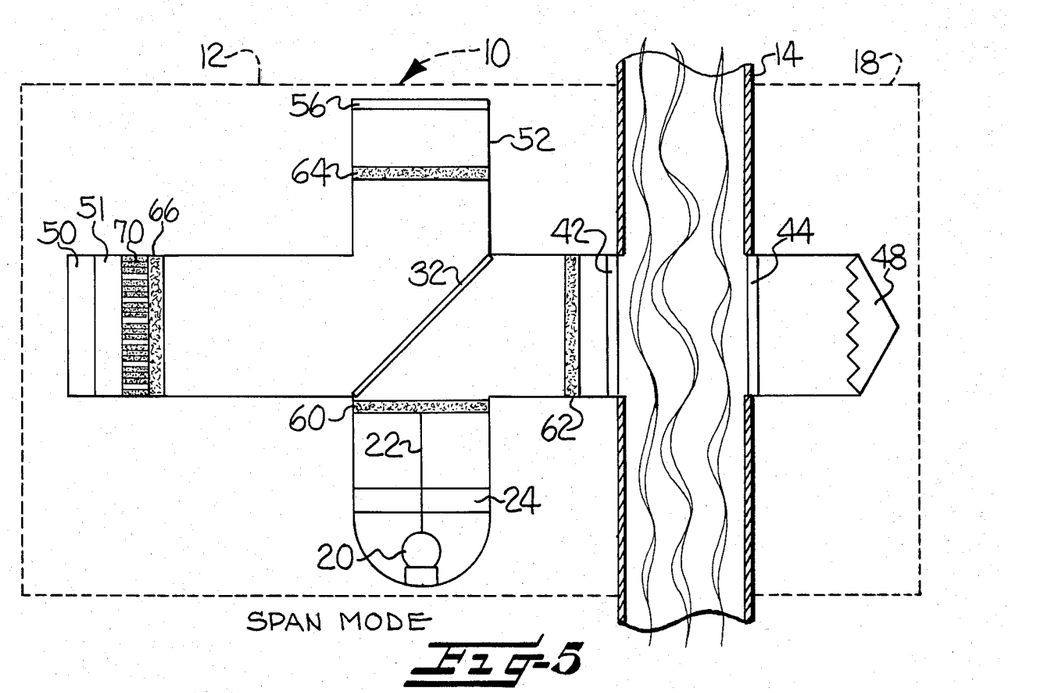
FIG. 5 is a view similar to FIGS. 2-4 showing the transmissometer in the span mode.

FIG. 5 illustrates the span mode that presents a "dark current" to the detector. Each of the electronic shutters 60, 62, 64, 66 is placed in its opaque condition and the stepwise attenuator 70 is put at its maximum opacity of 75% opaque. It will be appreciated that the light to photodetector 50 will be essentially blocked by the opaque condition of shutters 60, 62 and 64; however, span shutter 66, an optional but preferred element, helps assure that the photodetector indeed sees a dark current.

Figure 6:
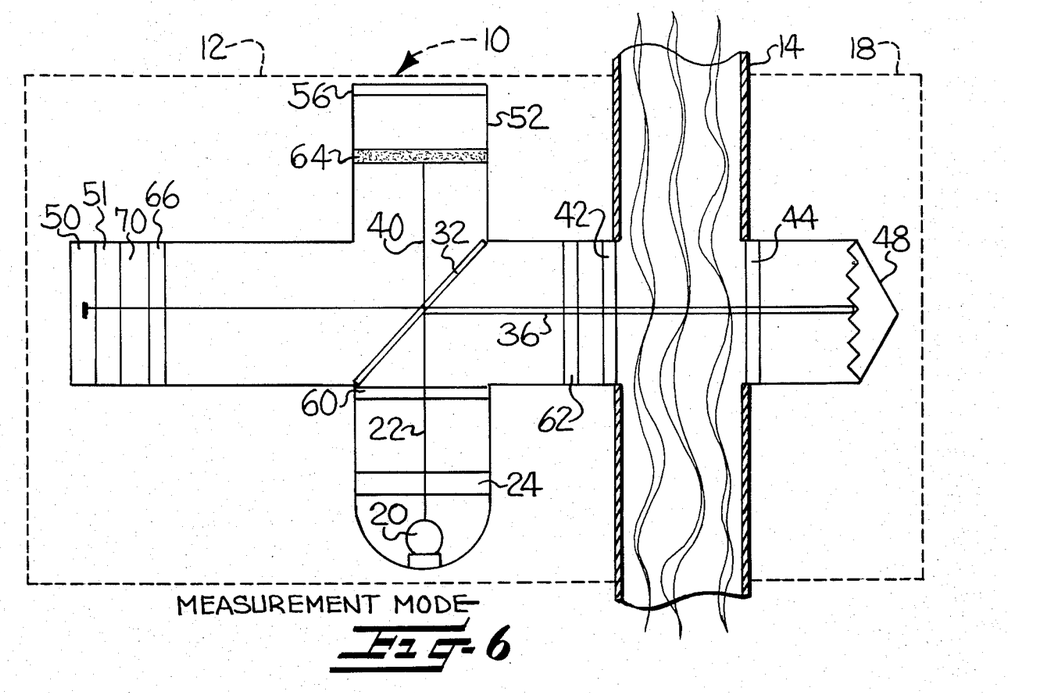
FIG. 6 is a view similar to FIGS. 2-5 showing the transmissomter in a measurement mode.

FIG. 6 illustrates the measurement mode wherein the reference beam is blocked by the opaque zero shutter 64 while allowing the transmitted beam to make a double pass through the smokestack and impinge upon photodetector 50. In the measurement mode, chopper shutter 60 is provided with an on-off pulse so that it alternates between clear and opaque, thus providing a comparison of the intensity of the reflected transmitted beam to the ambient light conditions at the photodetector.

Figure 13:
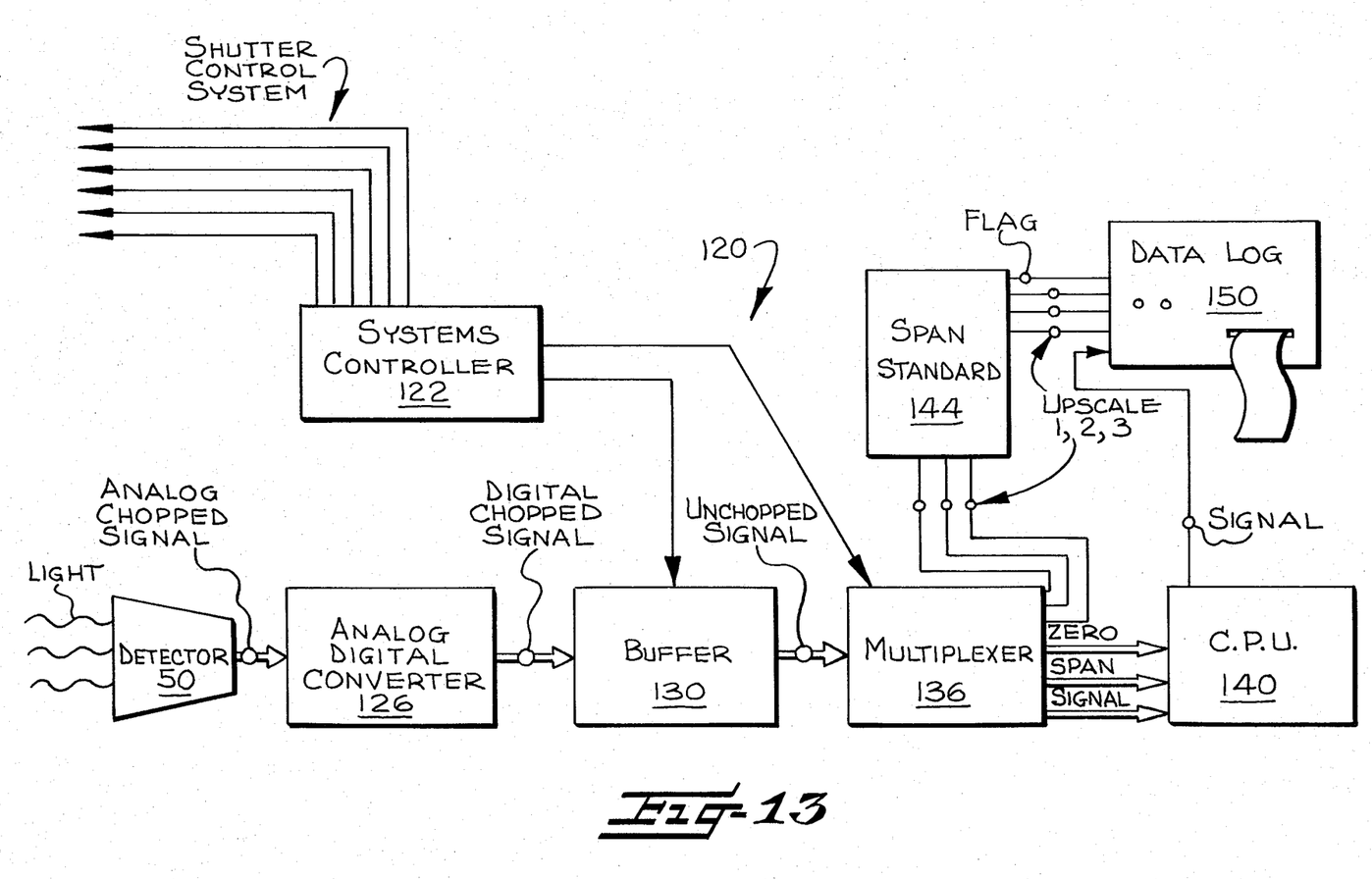
FIG. 13 is a block diagram of the signal flow chart for the transmissometer illustrated in FIGS. 1-6.

The signal conditioning circuit 120 of transmissometer 10 will now be described with reference to FIG. 13. Circuit 120 includes a system controller in the form of a solid state timer 122 that controls the states of shutters 60, 62, 64, 66 and attenuator 70 to place the transmissometer in the various modes discussed above, thereby determining the incident light on photodetector 50. The output of photodetector 50, in the form of an analog chopped signal, is directed to an analog/digital converter 126 that converts the signal to a digital chopped signal. This signal is conditioned to an unchopped signal by means of a buffer 130 and is fed to a multiplexer 136. Zero, span, measurement and upscale signals are received by a central processing unit 140 and a span standard 144, which together control the output of a data log 150.

The signals that are produced by photodetector 50 include: a simulated source zero signal (FIG. 3), upscale linearity check signals (FIG. 4), simulated source span signals (FIG. 5), measurement signals (FIG. 6) and ambient light interference signals (FIG. 6, with shutter 60 opaque and/or light 20 turned off). As noted above, these signals are generated at predetermined intervals controlled by system controller 122.

The purpose of the ambient light interference signal is to determine the light incident on photodetector 50 when no light is being received from the light source. The interference signal is, therefore, generated by light scattered into the transmissometer from the stack, and may be sunlight or other ambient light in the system. The ambient light would make the apparent transmission higher than the actual transmission of light through the smokestack. Therefore, the "off" portion of the chopped signal is subtracted from the "on" or "light" portion of the signal to give true system transmittance.

The purpose of the simulated source zero and simulated source span signals are to establish an electronic zero intersect and slope to convert the photodetector output signal to a transmission of light measurement, as well known in the art.

The three upscale linearity check signals that are produced by operation of stepwise light attenuator 70 serve to verify that the transmissometer is operating correctly and is linear. These values must fall within established limits or a flag will be placed on the data.

Conversion of data to opacity readings is performed according to the following formula, $100 - \%$ transmission $= \%$ opacity and is accomplished by a simple subtraction of the value of the transmissometer from 100 in digital systems, or by signal inversion in analog systems.

While the present invention has been described in connection with illustrated embodiments it will be appreciated that modifications may be made without departing from the true spirit and scope of the invention.

What is claimed is:

1. An optical device comprising means for establishing a transmitted beam and a reference beam, means for subjecting the transmitted beam to a sample condition for attenuation thereby, detector means positioned for receiving each of said beams and generating a signal representative of a condition of the beams, and an electronic stepwise light attenuator located in the path of the reference beam, said attentutor having an optical field and comprising multiple liquid crystal display elements, each element being substantially uniformly distributed throughout the optical field and being independently energizable to place it in either a clear or an opaque condition, said elements being so positioned as to cooperate in their respective clear/opaque conditions to produce stepwise attenuation of the reference beam at predetermined and repeatable opacity steps, including multiple intermediate values between 0% and 100% opacity.

2. An optical device as set forth in claim 1 including a zero shutter located in the path of said reference beam.

3. An optical device as set forth in claim 1 wherein the liquid crystal display elements are formed as alternating strips.

4. An optical device as set forth in claim 1 wherein the liquid crystal display elements are formed as concentric circles.

5. An optical device as set forth in claim 1 wherein the liquid crystal display elements are formed as radiating strips.

6. An optical device as set forth in claim 1 wherein the liquid crystal display elements are formed as spirals.

7. A transmissometer for continuously monitoring the opacity of gases passing through a duct, e.g. flue gases passing through a smokestack, and being characterized by non-mechanical electronic light interruption and attenuation for measurement and calibration purposes, said transmissometer comprising:
- a primary unit for delivering a collimated light beam across the duct and receiving a reflected beam from the opposite side of the duct, said primary unit being adapted for mounting on one side of the duct;
- a retroreflecting unit adapted for mounting on the opposite side of the duct from said primary unit and including retroreflecting means for reflecting the light beam emanating from the primary unit back to the primary unit by reflection substantially along the direction of incidence;
- said primary unit including:
    - a light source;
    - optical means associated with said light source for establishing a collimated light beam;
    - a beam splitter located in the path of said light beam and inclined with respect to the light beam to split the beam of light into (i) a transmitted beam that traverses the duct to said retroreflecting means and is reflected back to the primary unit and (ii) a reference beam;
    - a photodetector located in the path of both the reference beam and the reflected transmitted beam for generating a signal representative of the light incident thereon;
    - an electronic zero shutter comprising a liquid crystal display selectively energizable to produce either a clear or an opaque condition, said zero shutter being located in the path of the reference beam between said beam splitter and said photodetector;
    - a stepwise light attenuator located in the path of the light that constitutes the reference beam, said stepwise light attenuator comprising multiple electronic display elements each of which is selectively and independently energizable in cooperation with the other elements to produce stepwise attenuation of the reference beam at predetermined and repeatable opacity steps;
    - an electronic system shutter comprising a liquid crystal display selectively energizable to provide either a clear or an opaque condition, said system shutter being located in the path of the transmitted light beam between said beam splitter and said retroreflector means;
    - an electronic chopper shutter comprising a liquid crystal display selectively energizable to provide either a clear or an opaque condition, said chopper shutter being located between the light source and the beam splitter;
- controls means for selectively energizing the electronic shutters and stepwise light attenuator to establish various multiple modes of light interruption and attenuation for measurement and calibration purposes; and
- means for processing the signals generated by the photodetector in the various modes.

8. A transmissometer as set forth in claim 7 wherein the electronic display elements are formed as alternating strips.

9. A transmissometer as set forth in claim 7 wherein said beam splitter comprises a partial mirror inclined at approximately 45° to the collimated light beam emanating from said optical means to establish the transmitted beam in a direction substantially normal to such collimated light beam, and to establish the reference beam as a colinear continuation of the non-reflected portion of such collimated light beam.

10. A transmissometer as set forth in claim 9 wherein said primary unit includes branch means that is oriented substantially normal to the transmitted beam for receiving the reference beam after it passes through the beam splitter, said branch means including said zero shutter and a front surface mirror oriented normal to the reference beam for reflecting the reference beam back to the beam splitter partial mirror where a portion thereof is reflected to said photodetector along a path substantially colinear with that of the transmitted beam.

11. A transmissometer as set forth in claim 7 including an electronic span shutter comprising a liquid crystal display selectively energizable to produce either a clear or an opaque condition, said span shutter being located directly ahead of said photodetector.

12. A transmissometer of the type used for measuring the opacity of a sample and having a beam splitter establishing a transmitted beam and a reference beam, means for receiving the transmitted and reference beams and generating signals representative of the intensity of the light incident thereon, and beam shutters located at selected points in the optical paths of said beams for interrupting the beams to establish various transmissometer modes of operation, said shutters comprising electronic liquid crystal displays selectively energizable to produce either a clear or an opaque condition at each display at selected time intervals.

13. A transmissometer as set forth in claim 12 including an electronic stepwise light attenuator located at a selected location in the path of at least one of said beams, said attenuator comprising a body and multiple liquid crystal display segments distributed throughout the body, said segments defining segment sets that are independently energizable to place each segment set in either a clear or an opaque condition, thereby providing a light attenuator having stepwise opacity determined by the conditions of said segment sets.

14. An optical device comprising means for establishing a light beam, means for subjecting the light beam, or some divided portion thereof, to a sample condition for attenuation thereby, detector means for generating a signal representative of a condition of the beam, or portion thereof, and at least one beam shutter for interrupting the light beam, or portion thereof, to establish multiple modes of operation for said optical device, for example, measurement and calibration modes, said electronic shutter comprising an electronic liquid crystal display selectively energizable to produce either a clear or an opaque condition at selected time intervals.

15. A method of calibrating a transmissometer of the type that establishes a reference beam incident upon a photodetector thereof, said method comprising the steps of:

directing the reference beam of the transmissometer so that prior to reaching the photodetector it is incident upon an electronic stepwise light attenuator having multiple electronic display elements, wherein each element is substantially uniformly distributed throughout the optical field of the attenuator and each element is independently energizable to place it in either a clear or an opaque condition;

selectively energizing certain ones of said display elements at predetermined intervals so as to produce stepwise attenuation of the reference beam at predetermined and repeatable opacity steps, including multiple intermediate values between 0% and 100% opacity; and transmitting the signals generated by the photodetector to a location remote from the transmissometer and processing said signals to provide calibration for said transmissometer.

* * * * *